(12) United States Patent
Penka

(10) Patent No.: US 12,311,091 B2
(45) Date of Patent: May 27, 2025

(54) DEVICE FOR AUTOMATICALLY ESTABLISHING THE VENOUS INFLOW TO A BLOOD RESERVOIR OF AN EXTRACORPOREAL BLOOD CIRCULATION SYSTEM

(71) Applicant: LivaNova Deutschland GmbH, Munich (DE)

(72) Inventor: Ottmar Penka, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 824 days.

(21) Appl. No.: 17/532,479

(22) Filed: Nov. 22, 2021

(65) Prior Publication Data
US 2022/0080094 A1 Mar. 17, 2022

Related U.S. Application Data

(63) Continuation of application No. PCT/EP2019/067129, filed on Jun. 27, 2019.

(51) Int. Cl.
*A61M 1/36* (2006.01)
*A61M 39/28* (2006.01)

(52) U.S. Cl.
CPC ........ *A61M 1/3607* (2014.02); *A61M 1/3624* (2013.01); *A61M 1/3653* (2013.01);
(Continued)

(58) Field of Classification Search
CPC .............. A61M 1/3607; A61M 1/3624; A61M 1/3653; A61M 1/3663; A61M 1/367;
(Continued)

(56) References Cited

U.S. PATENT DOCUMENTS 4,464,164 A * 8/1984 Troutner ............... A61M 1/303
604/6.11
4,466,804 A * 8/1984 Hino ................... A61M 60/279
604/6.14

(Continued)

FOREIGN PATENT DOCUMENTS

EP 3165246 A1 5/2017
WO 0044415 A1 8/2000

OTHER PUBLICATIONS

International Search Report for International Application No. PCT/EP2019/067129, dated May 3, 2020.

*Primary Examiner* — Adam Marcetich
*Assistant Examiner* — Ted Yang
(74) *Attorney, Agent, or Firm* — Seager, Tufte & Wickhem LLP

(57) ABSTRACT

A device for establishing venous inflow to a blood reservoir of an extracorporeal blood circulation system includes a restricting unit for restricting a venous inflow line and a vacuum unit for supplying vacuum to the blood reservoir. The device includes a control unit that, upon setting the desired venous flow rate, automatically supplies a first actuating signal to the restricting unit for restricting venous inflow to the blood reservoir and supplies a second actuating signal to the vacuum unit for establishing a degree of vacuum within the blood reservoir, so as to achieve the set venous flow rate. The device includes a venous flow sensor.

6 Claims, 1 Drawing Sheet

(52) U.S. Cl.
CPC .......... *A61M 1/3663* (2013.01); *A61M 1/367* (2013.01); *A61M 39/281* (2013.01); *A61M 2205/3334* (2013.01)

(58) Field of Classification Search
CPC ........ A61M 39/281; A61M 2205/3334; A61M 1/74; A61M 1/743; A61M 1/3627; A61M 1/1601; A61M 1/3621
See application file for complete search history.

(56) References Cited

U.S. PATENT DOCUMENTS

| | | | | |
|---|---|---|---|---|
| 4,756,705 A * | 7/1988 | Beijbom | ......... | A61M 1/362263 |
| | | | | 96/219 |
| 5,055,198 A * | 10/1991 | Shettigar | ............... | A61M 1/631 |
| | | | | 604/35 |
| 5,120,303 A * | 6/1992 | Hombrouckx | ........ | A61M 1/306 |
| | | | | 604/6.11 |
| 5,178,603 A * | 1/1993 | Prince | ................... | A61M 1/308 |
| | | | | 604/6.11 |
| 5,186,431 A * | 2/1993 | Tamari | .................. | A61M 60/38 |
| | | | | 251/5 |
| 5,385,540 A * | 1/1995 | Abbott | ............ | A61M 1/362261 |
| | | | | 604/113 |
| 5,462,416 A * | 10/1995 | Dennehey | ........ | A61M 1/36224 |
| | | | | 604/153 |
| 5,645,540 A * | 7/1997 | Henniges | ................ | A61M 1/02 |
| | | | | 604/35 |
| 5,820,579 A * | 10/1998 | Plotkin | ............... | A61M 60/851 |
| | | | | 422/44 |
| 5,899,873 A * | 5/1999 | Jones | .................. | A61M 1/3664 |
| | | | | 165/186 |
| 5,928,180 A * | 7/1999 | Krivitski | ................. | A61M 1/16 |
| | | | | 210/85 |
| 6,017,493 A * | 1/2000 | Cambron | ............ | A61M 1/3638 |
| | | | | 604/6.15 |
| 6,024,692 A | 2/2000 | Dilling | | |
| 11,229,729 B2 * | 1/2022 | Knott | .................. | A61M 1/3667 |
| 2001/0050256 A1 * | 12/2001 | Krivitski | ............ | A61M 1/3663 |
| | | | | 600/504 |
| 2002/0085952 A1 * | 7/2002 | Ellingboe | ........... | A61M 1/3663 |
| | | | | 604/4.01 |
| 2002/0133066 A1 * | 9/2002 | Miller | .................. | A61B 5/0261 |
| | | | | 600/310 |
| 2003/0163078 A1 * | 8/2003 | Fallen | ................... | A61M 1/367 |
| | | | | 604/6.15 |
| 2006/0122558 A1 * | 6/2006 | Sherman | ................ | A61M 1/73 |
| | | | | 604/67 |
| 2008/0027368 A1 * | 1/2008 | Kollar | ................ | A61M 1/3621 |
| | | | | 604/6.14 |
| 2008/0078382 A1 * | 4/2008 | LeMahieu | ......... | A61M 16/0069 |
| | | | | 128/200.24 |
| 2012/0130299 A1 * | 5/2012 | Knott | .................. | A61M 1/3667 |
| | | | | 604/6.15 |
| 2018/0344912 A1 | 12/2018 | Turner | | |

* cited by examiner

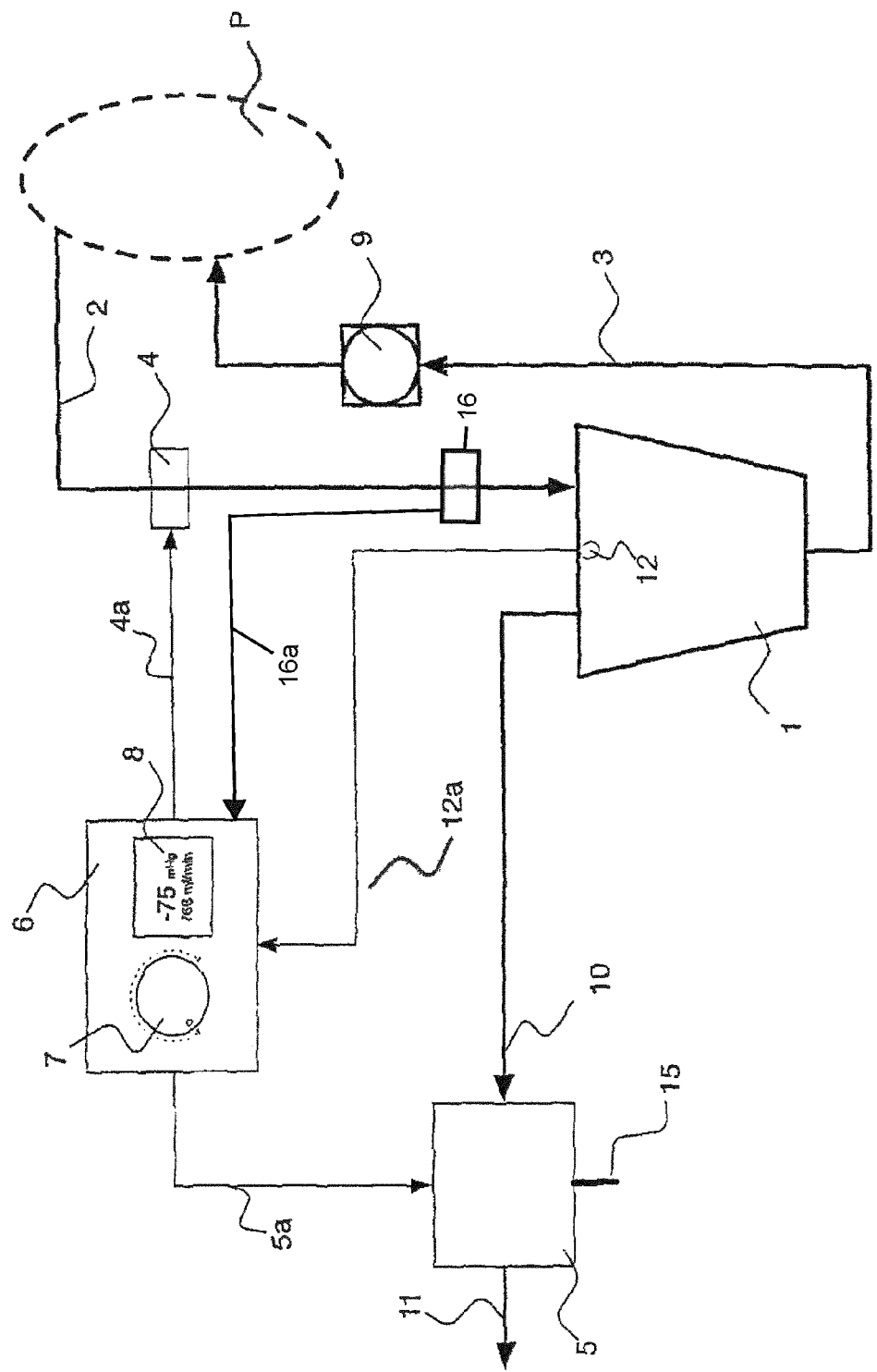

DEVICE FOR AUTOMATICALLY ESTABLISHING THE VENOUS INFLOW TO A BLOOD RESERVOIR OF AN EXTRACORPOREAL BLOOD CIRCULATION SYSTEM

CROSS REFERENCE TO RELATED APPLICATIONS

This application is a continuation of International Application No. PCT/EP2019/067129, filed Jun. 27, 2019, the disclosure of which is incorporated herein by reference.

TECHNICAL FIELD

The invention relates to a device for establishing venous inflow to a blood reservoir in an extracorporeal blood circulation system.

BACKGROUND

An extracorporeal blood circulation system often includes, in addition to other components, a venous inflow line from a patient to a blood reservoir, for example a venous/cardiotomy reservoir for blood and/or priming solution, and an arterial outflow line from the reservoir to the patient. In order to convey blood from the patient into the reservoir, the reservoir may be located at a lower level than the patient so that drainage can already occur by means of gravity. On the contrary, if the reservoir is located at a higher level than the patient, drainage can occur only with the assistance of the active action of a venous pump extracting blood from the patient or of a vacuum applied to the reservoir. Using a blood pump, a roller or a centrifugal pump, the blood is conveyed out of the reservoir through the arterial outflow line and is delivered to the patient.

So that the venous inflow to the reservoir occurs to a sufficient extent, large tube cross-sections and appropriate lengths, are required in the case of pure gravitational drainage. In case of pure gravitational drainage, the easiest way to influence venous inflow is to act on the venous line cross section by changing it. Another possibility is given by altering the difference in height between the reservoir and the patient, but this cannot be easily done during use, while maintaining the extracorporeal blood circulation.

As is described, for example, in WO 00/44415 A, it has already been proposed to apply a vacuum to the reservoir in order to reduce the cross-section and/or length of the drainage line, or to reduce the height difference between the patient and the reservoir and to be able to influence the venous inflow. In this case, venous inflow is determined by the amount of vacuum applied to the reservoir, i.e., the patient is drained by means of the so-called vacuum assisted venous drainage (VAVD). In this regard, WO 00/44415 A discloses a vacuum regulator attached to the reservoir, that simplifies management of the vacuum by the user so as to increase patient safety during an operation. The reason for this is that a reliable regulation of the vacuum first of all enables a simple adjustment of the vacuum by a user and thus a simple adjustment of the venous inflow. A reliable regulation of the vacuum also prevents a vacuum which is too high and which presents a danger to the patient, as it may cause the collapse of the vessels at the venous cannulation site, due to excessive drainage. In WO 00/44415 A, previously known solutions are referred to as being insufficient and an independent device for regulating the vacuum is described, which reliably regulates the vacuum in the reservoir and optionally also reduces it should this be necessary.

When supplying blood from the reservoir to the patient, care must be taken to ensure that no more blood is removed from the reservoir than is present therein or is supplied thereto. The user must therefore make sure that there is a sufficient minimum amount in the reservoir and additionally coordinate the inflow and outflow such that sufficient amounts are built up in the reservoir but are also supplied to the patient since a physiologically sufficient supply of the patient must always be ensured in an extracorporeal blood circulation system. When draining the patient by gravity, the user may thereby, for example, increase or reduce the delivery rate of the outflow pump, and/or he may also reduce/increase the line cross-section of the venous line by means of clamping and/or unclamping it. In alternative, if blood is drained by vacuum (i.e. in VAVD), the user, besides adjusting the outflow pump delivery rate according to the perfusion needs, must pay attention to the amount of drained blood and suitably adjust the vacuum in the reservoir—even in the aforementioned vacuum regulator. The user must meet this requirement in an environment which furthermore compels him, in all of his actions, to pay attention to the surgical operation supported by the extracorporeal circulation. Overall, the adjustment of the venous inflow amount to the reservoir of an extracorporeal blood circulation system therefore occurs in a stressful working environment, and thus the previous technical solutions for supporting the user in the adjustment of the venous inflow amount to the reservoir must be regarded as sub-optimal.

Against this background, the technical problem to be solved by the invention is to specify a device for establishing the venous inflow to a blood reservoir of an extracorporeal blood circulation system, which further simplifies the management of the extracorporeal blood circulation system for the user.

SUMMARY

A device as according to the invention for establishing the venous inflow to a blood reservoir of an extracorporeal blood circulation system, which includes a venous inflow line from a patient to the reservoir and an arterial outflow line from the reservoir to the patient, further includes, in addition to a restricting unit for restricting (e.g., by gradually closing), in particular clamping, the venous inflow line in order to restrict the venous inflow amount to the reservoir and a vacuum unit for applying a vacuum to the reservoir in order to increase the venous inflow amount to the reservoir, a control means which supplies to the restricting unit a first actuating signal for establishing the degree of closure of the venous inflow line in order to determine the extent of the restriction of the venous inflow amount to the reservoir, and which supplies to the vacuum unit a second actuating signal for establishing the amount of vacuum in the reservoir in order to determine the extent of the increase in the venous inflow amount to the reservoir, and which includes a single operating element for setting of the amount of venous inflow to the reservoir by a user.

By providing a single operating element for setting of the amount of venous inflow to the reservoir by a user, the user is given the opportunity in a simple manner to determine the venous inflow to the reservoir at, above and below a basic value, corresponding to the conditions of unrestricted venous line and open to ambient pressure reservoir, by a single adjustment process. That is, the basic value is a value established by gravitational conveyance while the inflow line is not restricted by the restricting unit. Settings of venous flow rates below the basic value can be achieved by restricting the venous line, while settings above the basic value can be achieved by applying vacuum to the reservoir. As a result of the configuration of the control means according to the invention, it is achieved that the device according to the invention appropriately adjusts and regulates the venous inflow. It should be noted that the single operating element described above and in the following is solely for the function of setting the amount of venous inflow to the reservoir by a user. The control means can additionally include further operating elements, such as, for example, an on/off switch, a brightness regulator for optionally provided displays, a selector switch for activating/deactivating an alarm, etc. However, according to some embodiments of the invention, only one single operating element is provided for setting of the amount of venous inflow to the reservoir by a user, said element allowing setting of the venous inflow both at above and below a basic value, as defined previously.

In some embodiments, the control means includes a display device for visual display of a display value corresponding to the amount of venous inflow. By means of this display providing an indication of value as regards the venous inflow, the vacuum in the reservoir and/or the venous line cross section restriction may also be displayed.

In some embodiments, the vacuum unit is connected to a vacuum source via a line or alternatively or additionally includes an integrated vacuum source, in particular a vacuum pump.

In some embodiments, a vacuum sensor for detecting the vacuum in the reservoir is provided, which is connected to the control means for providing a corresponding measuring signal.

In some embodiments, the vacuum unit includes a safety device which, upon actuation by the control means or if control should fail, interrupts the application of a vacuum to the reservoir and establishes atmospheric pressure in the reservoir.

The device includes a venous flow sensor disposed on the venous inflow line and configured to measure a venous flow rate of the circulating blood in the venous inflow line and to send a venous flow rate signal representing the venous flow rate to the control device.

In some embodiments, the control device is configured to automatically determine a flow rate adjustment value based on the venous flow rate measured by the venous flow sensor. For example, the flow rate adjustment value may correspond to a difference between a set value and a measured value.

BRIEF DESCRIPTION OF THE DRAWINGS

The invention will be described in more detail in the following with reference to the drawing, in which:

FIG. 1 shows a view of the basic structure of an extracorporeal blood circulation system having a device according to a first embodiment of the invention.

DETAILED DESCRIPTION

As is shown in FIG. 1 by means of a first embodiment of a device according to the invention, an extracorporeal blood circulation system basically includes, in addition to a reservoir 1, a venous inflow line 2 from a patient P to the reservoir 1 and an arterial outflow line 3 from the reservoir 1 to the patient P. In order to supply blood from the reservoir 1 to the patient P, a pump 9, such as a roller pump or a centrifugal pump, is provided on or in the arterial outflow line 3. As is apparent from FIG. 1, the reservoir 1 is located at a lower level than the patient so that a venous inflow to the reservoir is already possible owing to gravity alone, the extent of which also depends, however, on the cross-section and the length of the tube used in the venous inflow, besides the height difference between patient and reservoir.

In order to restrict the venous inflow to the reservoir 1 below the basic value, the first embodiment of the invention as described herein includes a restricting unit 4, by which the venous inflow line 2 can be restricted (e.g., by being gradually closed), for example by clamping or squeezing. For this purpose, the restricting unit 4 includes an electromagnetically, pneumatically or hydraulically-operated clamp which is not shown in detail in FIG. 1. The restricting unit 4 is arranged on the venous inflow line 2 and in some embodiments acts externally on the tube without coming into contact with the blood. If the venous line is unrestricted by the restricting unit 4 and no vacuum is applied to the reservoir, the venous inflow is at its basic value.

In order to increase the venous inflow to the reservoir 1 above the basic value, the first embodiment of a device according to the invention includes a vacuum unit 5 for applying a vacuum to the reservoir 1. For this purpose, the vacuum unit 5 is connected via a vacuum line 10 to the reservoir 1 which is accordingly designed so as to become pressure-tight, when vacuum is applied. If the vacuum unit 5 is itself not configured for generating the vacuum, for example by integration of a suitable pump, the vacuum unit 5, as is the case in the first embodiment shown in FIG. 1, is connected to a vacuum source via a vacuum source line 11. Suitable vacuum sources are generally available in the form of stationary installations in hospitals where the device according to the invention is primarily used.

According to the invention, the setting of the venous inflow by the user occurs in a simple and comfortable yet also safe manner via a control means 6 (e.g., a control device) which is shown in FIG. 1. The control means 6 supplies to the restricting unit 4, via a first actuation line 4a, a first actuating signal for establishing the degree of closure of the venous supply line 2 in order to carry out restriction of the venous inflow amount to the reservoir below the basic value. The control means 6 furthermore supplies to the vacuum unit 5, via a second actuation line 5 a, a second actuating signal for establishing the amount of vacuum in the reservoir 1 in order to carry out an increase in the venous inflow amount to the reservoir above the basic value. In embodiments, one or more of the actuation lines 4a and 5a can be implemented as analogue or digital signals, as carriers or analogue or digital signals, as a digital bus system, and/or the like.

According to the invention, the control means 6 includes a single operating element 7 for setting of the amount of venous inflow to the reservoir by a user of the device. Solely by actuating this single operating element 7, the user can set the venous inflow amount to the reservoir 1 and thereby undertake both an increase to beyond the amount which is essentially determined by the gravitational drainage, the length and the cross-section of the tube used on the venous side, as well as a reduction to below this value. The control means 6 according to the invention converts the setting carried out by the user by means of the single operating element 7 into a corresponding actuation of the restricting unit 4 or the vacuum unit 5 so as to thereby cause a reduction of the venous inflow below the gravitational amount by closing (clamping) the venous inflow tube line 2, or alternatively, an increase above the gravitational amount in the venous inflow by creating a vacuum in the reservoir 1. In some examples, the single operating element 7 may be a control knob and/or a control interface.

As is shown by FIG. 1, the first embodiment includes a pressure sensor 12, which is arranged on or in the reservoir 1 so as to detect the vacuum in the reservoir 1 and provide a corresponding first measuring signal. The measuring signal of the vacuum sensor 12 is supplied via a first measuring signal line 12a to the control means 6, which can carry out regulation of the vacuum taking into account this measured value. In embodiments, the vacuum sensor 12 may also be connected directly to the vacuum line 10.

The control means 6 according to the first embodiment furthermore includes a display 8 which indicates to the user the set venous inflow amount and/or the percentage tube occlusion and/or the reservoir vacuum. In embodiments, the functionality of the control means 6 and the vacuum unit 5 may be included in one single unit or may be distributed across various physical devices which communicate with each other.

As is shown by FIG. 1, the first embodiment includes a sensor 16 (e.g., a flow sensor), which is arranged or disposed on the venous inflow tube line 2, such as between the restricting unit 4 and the reservoir 1. In certain examples, the sensor 16 may be disposed on the inflow tube line 2 between the restricting unit 4 and the patient P. The sensor 16 is configured to measure a venous flow rate (e.g., volumetric flow rate) of the circulating blood in the venous inflow tube line 2.

In various examples, the sensor 16 is coupled (e.g., operatively, communicatively, electrically, and/or electronically) to the restricting unit 4, the vacuum unit 5, and/or the control means 6. For example, the sensor 16 may be configured to send a flow rate signal (e.g., representing or corresponding the flow rate of the circulating blood in the venous inflow tube line 2) to the control means 6, such as continuously or intermittently. In certain embodiments, the control means 6 is configured to determine a flow rate adjustment value and to send a flow rate adjustment signal (e.g., representing the flow rate adjustment value) to the restricting unit 4 and/or the vacuum unit 5. In some examples, the flow rate adjustment value corresponds to the difference between the flow rate measured by the sensor and a target flow rate (e.g., set via the single operating element 7). In various embodiments, the restricting unit 4 (e.g., a clamp) is configured to be electronically controlled, modified, manipulated, and/or adjusted, such as to be automatically adjusted (e.g., by the control means 6) in response to the venous flow rate measured by the sensor 16. The sensor 16 outputs a measuring signal (e.g., representing the measured flow rate) that is supplied to the control means 6 via a measuring signal line 16a. That is, for example, if the measured (by the sensor 16) venous flow rate is higher than the set value (target flow rate), then the control means 6 acts on the restricting unit 4 by causing it to restrict the line 2 until the set value and the measured value are equal (or at least approximately equal).

In certain examples, the restricting unit 4 is configured to reduce restriction (e.g., automatically) if flow rate is to be increased at the venous inflow tube line 2. For example, the restricting unit 4 is configured to reduce restriction (e.g., automatically) upon receiving a flow rate adjustment signal representing a positive flow rate adjustment value (e.g., when measured flow rate is less than the target flow rate). In certain examples, the restricting unit 4 is configured to increase restriction (e.g., automatically) if flow rate is to be decreased at the venous inflow tube line 2. For example, the restricting unit 4 may be configured to increase restriction (e.g., automatically) upon receiving a flow rate adjustment signal representing a negative flow rate adjustment value (e.g., when measured flow rate is greater than the target flow rate). In various examples, the restricting unit 4 is configured to both increase and reduce restriction in response to the flow rate measured by the sensor 16, such as automatically increase and/or reduce. In some examples, the restricting unit 4 (e.g., a restrictor) is configured to be adjustable from 0% open (i.e., 100% closed) to 100% open (i.e., 0% closed), such as continuously or step-wisely adjustable.

In various embodiments, the vacuum unit 5 is configured to be electronically controlled, modified, manipulated, and/or adjusted, such as to be automatically adjusted (e.g., by the control means 6) in response to the venous flow rate measured by the sensor 16. In certain examples, the vacuum unit 5 is configured to reduce pressure (e.g., automatically) in the reservoir 1 (e.g., increase vacuum level) if flow rate is to be increased at the venous inflow tube line 2. For example, the vacuum unit 5 is configured to reduce pressure (e.g., automatically) in the reservoir 1 (e.g., increase vacuum level) upon receiving a flow rate adjustment signal representing a positive flow rate adjustment value (e.g., when measured flow rate is less than the target flow rate). In certain examples, the vacuum unit 5 is configured to increase pressure (e.g., automatically) in the reservoir 1 (e.g., reduce vacuum level) if flow rate is to be decreased at the venous inflow tube line 2. For example, the vacuum unit 5 may be configured to increase pressure (e.g., automatically) in the reservoir 1 (e.g., reduce vacuum level) upon receiving a flow rate adjustment signal representing a negative flow rate adjustment value (e.g., when measured flow rate is greater than the target flow rate). In various examples, the vacuum unit 5 is configured to both increase and reduce pressure in the reservoir 1 in response to the flow rate measured by the sensor 16, such as automatically increase and/or reduce. That is, if the measured flow value is lower than the set value, the control means 6 causes the restricting unit 4 to unclamp the line 2 until the line gets fully open, and if the set value is still higher than the measured value, the control means 6 causes vacuum to be applied, via the vacuum unit 5, to the reservoir until the set and measured values are equal (or at least approximately equal).

In some embodiments, the restricting unit 4 and the vacuum unit 5 are configured to dynamically controlled and/or adjusted in response to a flow rate adjustment value. For example, the control means 6 may be configured to send (e.g., automatically) a first flow rate adjustment signal to the restricting unit 4 and to send a second flow rate adjustment signal to the vacuum unit 5 to jointly adjust the flow rate from the measured flow rate (e.g., measured by sensor 16) to the target flow rate (e.g., set via the single operating element 7). In certain examples, the control means 6 is configured to automatically determine whether to send a flow rate adjustment signal to the restricting unit 4 and/or to send a flow rate adjustment signal to the vacuum unit 5. In some examples, the restricting unit 4 is configured to adjust flow rate (e.g., in the venous inflow tube line 2) within a first flow rate range (below gravitational value), with a first response time, at a first sensitivity, and/or at a first accuracy. In some examples, the vacuum unit 5 is configured to adjust flow rate (e.g., in the venous inflow tube line 2) within a second flow rate range (above gravitational value), with a second response time, at a second sensitivity, and/or at a second accuracy. In certain embodiments, the control means 6 is configured to automatically determine where to send its one or more flow rate adjustment signals, based on one or more of target flow rate range, flow rate adjustment magnitude, target response time, target sensitivity, and target accuracy. For example, in case the reservoir is placed at the same level of the patient or higher than the patient, there is little or no gravitational drainage; therefore, the set value is almost always higher than the measured value, which requires that the line be fully open and vacuum be applied to the reservoir so that the set and the measured values become equal or at least approximately equal.

As is shown in FIG. 1, the vacuum unit 5 can be equipped in all of the embodiments with a safety device 15 which, upon corresponding actuation by the control means 6 or if control should fail, interrupts the application of a vacuum to the reservoir 1 and establishes atmospheric pressure in the reservoir 1.

I claim:

1. A device for establishing venous inflow to a blood reservoir of an extracorporeal blood circulation system including a venous inflow line from a patient to the blood reservoir and an arterial outflow line extending from the blood reservoir to the patient, the device comprising:
   a restricting unit configured for clamping the venous inflow line in order to act on the venous inflow amount to the blood reservoir in the range below a basic value, the basic value comprising a value established by gravitational conveyance while the inflow line is not restricted by the restricting unit;
   a vacuum unit configured for applying a vacuum to the blood reservoir in order to act on the venous inflow amount to the blood reservoir in the range above the basic value;
   a control device that includes a single operating element having a plurality of operating positions and configured to be manipulated in a single manipulation by a user to establish both a degree of closure of the venous inflow line and an amount of vacuum in the blood reservoir for venous inflow to the blood reservoir at, above or below the basic value; and
   a venous flow sensor disposed on the venous inflow line and configured to measure a venous flow rate of the circulating blood in the venous inflow line and to send a venous flow rate signal representing the venous flow rate to the control device;
   wherein, at each operating position of the plurality of operating positions, the control device is configured to supply a different combination of a restricting unit setting that corresponds to an extent of a restriction of the venous inflow amount to the blood reservoir below the basic value, based on the manipulation of the single operating element in the single manipulation and a vacuum unit setting that corresponds to the operating position to the vacuum unit for establishing the amount of vacuum in the blood reservoir to define an extent of the increase in the venous inflow amount to the blood reservoir above the basic value based on the manipulation of the single operating element in the single manipulation, without the use of a blood level sensor and blood level signals;
   wherein the control device is configured to automatically determine a first flow rate adjustment value based on the venous flow rate measured by the venous flow sensor and the selected operating position;
   wherein the control device is configured to automatically send a first flow rate adjustment signal to the restricting unit and a second flow rate adjustment signal to the vacuum unit such that the restricting unit adjusts the degree of closure at the venous inflow line and the vacuum unit adjusts the amount of vacuum in the blood reservoir to collectively adjust the flow rate of the circulating blood in the venous inflow line by the two flow rate adjustment values.

2. The device according to claim 1, wherein the control device further comprises a display device for visual display of a display value corresponding to the venous inflow amount.

3. The device according to claim 1, wherein the vacuum unit is connected to a vacuum source via a line.

4. The device according to claim 1, wherein the vacuum unit comprises an integrated vacuum source.

5. The device according to claim 1, further comprising a vacuum sensor for detecting a vacuum in the blood reservoir, the vacuum sensor connected to the control-device for providing a first measuring signal.

6. The device according to claim 1, wherein the vacuum unit further comprises a safety device configured such that, upon actuation by the control device or upon failure of the control device, an application of a vacuum to the blood reservoir is interrupted which establishes atmospheric pressure in the blood reservoir.

* * * * *